(12) United States Patent
Walle et al.

(10) Patent No.: US 6,515,284 B1
(45) Date of Patent: Feb. 4, 2003

(54) PROCESSES AND DEVICES FOR THE PHOTOTHERMAL INSPECTION OF A TEST BODY

(75) Inventors: Günter Walle, Mandelbachtal (DE); Udo Netzelmann, Säärbücken (DE); Thomas Vetterlein, Offenbach am Main (DE)

(73) Assignee: Fraunhofer-Gesellschaft zur Forderung der Angewandten Forschvng E.V., München (DE)

( * ) Notice: Subject to any disclaimer, the term of this patent is extended or adjusted under 35 U.S.C. 154(b) by 0 days.

(21) Appl. No.: 09/530,847
(22) PCT Filed: Oct. 27, 1998
(86) PCT No.: PCT/DE98/03137
§ 371 (c)(1),
(2), (4) Date: May 26, 2000
(87) PCT Pub. No.: WO99/24814
PCT Pub. Date: May 20, 1999

(30) Foreign Application Priority Data

Nov. 12, 1997 (DE) ......................... 197 49 984

(51) Int. Cl.$^7$ .................................................. G01N 21/71
(52) U.S. Cl. .................................................. 250/341.6
(58) Field of Search ..................................... 250/341.6

(56) References Cited

U.S. PATENT DOCUMENTS

| | | | |
|---|---|---|---|
| 3,451,254 A | | 6/1969 | Maley |
| 4,965,451 A | * | 10/1990 | Sölter ........................ 250/330 |
| 5,444,241 A | * | 8/1995 | Del Grande et al. ........ 250/253 |
| 5,667,300 A | | 9/1997 | Mandelis et al. |
| 2001/0042833 A1 | * | 11/2001 | Kenway .................. 250/341.6 |

FOREIGN PATENT DOCUMENTS

| | | |
|---|---|---|
| DE | 38 20 862 A1 | 12/1989 |
| DE | 195 20 788 A1 | 7/1996 |
| JP | 09 159631 | 6/1997 |
| WO | WO98/05921 A1 | 2/1998 |

OTHER PUBLICATIONS

Almond D.P. Edge–effects and defect sizing by transient thermography, QIRT 94 –Eurotherm Series 42 –EETI ed., Paris 1995.

* cited by examiner

*Primary Examiner*—Constantine Hannaher
(74) *Attorney, Agent, or Firm*—Oppedahl & Larson LLP

(57) ABSTRACT

Processes and devices for the photothermal inspection of a test body. Lighting radiation with short lighting times is applied to a test body and at least one measurement value of the emission curve during or after a short lighting time is sensed. The diffusion and/or effusion capacity of a test body coating layer, for example, can be determined by computer units on the basis of the measurement value(s), even when the thickness of the coating layer is unknown, because the measurement values are detected during or shortly after irradiation and the coating layer thickness plays only an insignificant role in the course of the emission curve in this range.

12 Claims, 8 Drawing Sheets

PROCESSES AND DEVICES FOR THE PHOTOTHERMAL INSPECTION OF A TEST BODY

The invention relates to processes for photothermally inspecting a test specimen in which the test specimen is acted on by luminous radiation in an illumination region during an illumination time and thermal radiation emitted by the test specimen from a detection region is detected in a time-resolved manner, wherein properties of the test specimen are determined from the chronological course of the thermal radiation, which can be represented by means of an emissions curve that has a heating part with an increasing amplitude and a cooling part with a decreasing amplitude.

The invention also relates to devices for photothermally inspecting a test specimen, having an illumination device with which the test specimen can be acted on by luminous radiation in an illumination region during an illumination time and having a detection device with which thermal radiation emitted by the test specimen from a detection region can be detected in a time-resolved manner, and having a control and evaluation device with which properties of the test specimen can be determined from the chronological course of the thermal radiation, which can be represented by means of an emissions curve that has a heating part with an increasing amplitude and a cooling part with a decreasing amplitude.

Processes and devices of this kind have been disclosed by DE 38 20 862 A1. An illumination device acts on a test specimen with luminous radiation in an illumination region during an illumination time. A detection device is used to carry out a time-resolved detection of thermal radiation emitted by the test specimen from a detection region. When plotting a temperature in relation to time, the thermal radiation detected can be represented by an emissions curve that has a heating part with an increasing amplitude and a cooling part with a decreasing amplitude, wherein properties of the test specimen can be determined from chronological correlations between the impingement of luminous radiation on the test specimen and the course of the emissions curve. With the processes and devices of this generic type, in order to detect errors, determinations are made as to deviations of emissions measurement curves from emissions model curves that are calculated from preset parameters such as thermal conductivity, absorption coefficient, and/or emissions coefficient.

U.S. Pat. No. 4,679,946 has disclosed a process and a device for determining both a layer thickness and material parameters of a coating-like test specimen, in which the test specimen is acted on by luminous radiation and thermal radiation emitted by it is detected. Two measurement processes functioning independently of each other are used for this purpose, wherein on the one hand, thermal signals associated with a surface temperature and on the other hand, signals that exist chiefly as a function of the temperature underneath the surface are detected and processed. Through the use of a dual-segment detector, these two types of signals can be simultaneously detected independently of each other. However, this device requires two radiation sources embodied in the form of lasers as well as the specially designed detector element.

The object of the invention is to disclose processes and devices of the type mentioned the beginning with which the material properties of the test specimen can be determined in a relatively precise manner in a way that does not involve expensive equipment, even without knowledge of exact layer thicknesses.

This object is attained with the process mentioned at the beginning in an embodiment of a first type by virtue of the fact that a pulse-like illumination time is set, which is less than the quotient of the square of an estimated value of a layer thickness constituted by the distance between boundary surfaces and an estimated value for the diffusivity between the boundary surfaces and that the effusivity of the test specimen is determined from at least one measurement value disposed in the heating part or in a section of the cooling part immediately following the heating part, which has a high cooling rate that corresponds to a heating rate of the heating part.

This object is attained with the device mentioned at the beginning in an embodiment of a first type by virtue of the fact that the illumination device can set at least one illumination time that is less than the quotient of the square of an estimated value of a layer thickness constituted by the distance between boundary surfaces and an estimated value for the diffusivity between the boundary surfaces and that a calculating unit is provided, with which the effusivity of the test specimen can be determined from at least one measurement value disposed in the heating part or in a section of the cooling part immediately following the heating part, which has a high cooling rate that corresponds to a heating rate of the heating part.

With the process and device of the first type, since at least one measurement value within the very short heating part or in the partial section of the emissions curve immediately following the end of the pulse-like illumination is detected in accordance with the knowledge underlying the invention that with pulse-like illumination in this region of the emissions curve, the influence of the layer thickness on the measurement of material properties is negligible, material properties can be determined very precisely from at least one measurement value, even without knowledge of the layer thickness.

This object is also attained with the process mentioned at the beginning in an embodiment of a second type by virtue of the fact that at least two illumination times are set, which are less than the quotient of the square of an estimated value for a layer thickness of the coating and an estimated value for the diffusivity of the coating, that the illumination region and the detection region are spaced apart from each other with a diffusion spacing, that the maximal amplitudes are determined for each emissions curve, which maximal amplitudes occur for each illumination time in the detection region, with associated adjustment times, and that the diffusivity is determined from the ratio between at least two maximal amplitudes, the diffusion spacing, and the associated adjustment times.

This object is also attained with the device mentioned at the beginning in an embodiment of a second type by virtue of the fact that the illumination device can set at least two illumination times, which are less than the quotient of the square of an estimated value of a layer thickness constituted by the distance between boundary surfaces and an estimated value for the diffusivity between the boundary surfaces, that the illumination region and the detection region are spaced apart from each other with a diffusion spacing, that an emissions maximum locating unit can determine maximal amplitudes of each emissions curve which occur for each illumination time in the detection region, with associated adjustment times, and that a diffusivity calculation unit can determine a diffusivity from the ratio between two maximal amplitudes, the diffusion spacing, and the associated adjustment times.

With the process and device of the second type, since after a relatively short pulse-like heating, the propagation of thermal waves beyond the maximal amplitudes of emissions curves is detected after illuminations of different lengths, when the diffusion spacing is known, the diffusivity can be determined independently of the power density of the luminous radiation.

In suitable modifications of the process and the device of the first type, after the effusivity has been determined, the layer thickness is also determined, which can be ascertained from the long-term course of the emissions curve.

In order to increase the measurement precision of the effusivity, modifications of the process and device of the first type provide that a number of emissions measurement values are detected in the heating part of the emissions curve or in the cooling part immediately following the heating part and are compared to the standard of emissions model curves calculated from model parameters, wherein the material properties can be derived from the emissions model curve with the least deviations from the measurement values.

In suitable modifications of the process and device of the second type, two illuminations are provided, preferably with illumination times that differ by a factor of two, wherein the longer illumination time is half the quotient of the square of the estimated value for a layer thickness of a coating and the estimated value for the diffusivity of the coating. This assures that the influence of the layer thickness is negligible.

In order to explain the physical interrelationships in the process and device of the first type, some determination equations will be given below.

The effusivity is the root of the product of the thermal conductivity, the density, and the specific heat capacity. Diffusivity is understood to mean the quotient of the thermal conductivity and the specific heat capacity multiplied by the density.

For example, the non-stationary thermal conduction theory yields the following temperature course, which represents an emissions curve, at the surface of a test specimen for the heating part and the early cooling part after the end of illumination with a short rectangular pulse:

$$T(z=0, t) = \frac{2F_0}{\sqrt{\pi}} \cdot \frac{1}{E} \cdot \begin{cases} \sqrt{t} & \text{for } 0 \le t \le t_p \\ (\sqrt{t} - \sqrt{t-t_p}) & \text{for } t \ge t_p \end{cases} \quad (1)$$

wherein $T(z=0, t)$ is the temperature at the surface of the test specimen, $F_0$ stands for the introduced power density in $W/cm^2$, E stands for the effusivity, $t_P$ represents the illumination time, and t represents the time since the beginning of the illumination. With the detection of one or a number of emissions measurement values at known times $t_i$ which lie in the heating part of the emissions curve or in the early cooling part immediately following the heating part, as well as the associated temperatures $T_i$, if the power density $F_0$ is known, the above equation can be used to determine the effusivity, independent of the layer thickness.

With the process and device of the second type, the determination of the diffusivity is based on the following equation:

$$\frac{T_1}{T_2} = \frac{\text{erfc}\frac{r}{\sqrt{4\alpha t_1}}}{\text{erfc}\frac{r}{\sqrt{4\alpha t_2}}} \quad (2)$$

wherein $T_1$, $T_2$ stand for the temperatures occurring after illumination with illumination times $t_1$, $t_2$ in a diffusion spacing r from the illumination region, $\alpha$ stands for the diffusivity, and "erfc" stands for the so-called complementary Gaussian error function in the form:

$$\text{erfc}(x) = 1 - \frac{2}{\sqrt{\pi}} \int_0^x e^{-y^2} dy \quad (3)$$

Through variation of the diffusivity $\alpha$, the equation (2), which has one value due to the temperature measurement, the knowledge of the diffusion spacing, and the knowledge of the illumination times, can be fulfilled with a diffusivity $\alpha$.

Other suitable embodiments and advantages of the invention are the subject of the dependent claims as well as the subsequent description of exemplary embodiments taken in consideration with the figures of the drawings.

Figure 7:
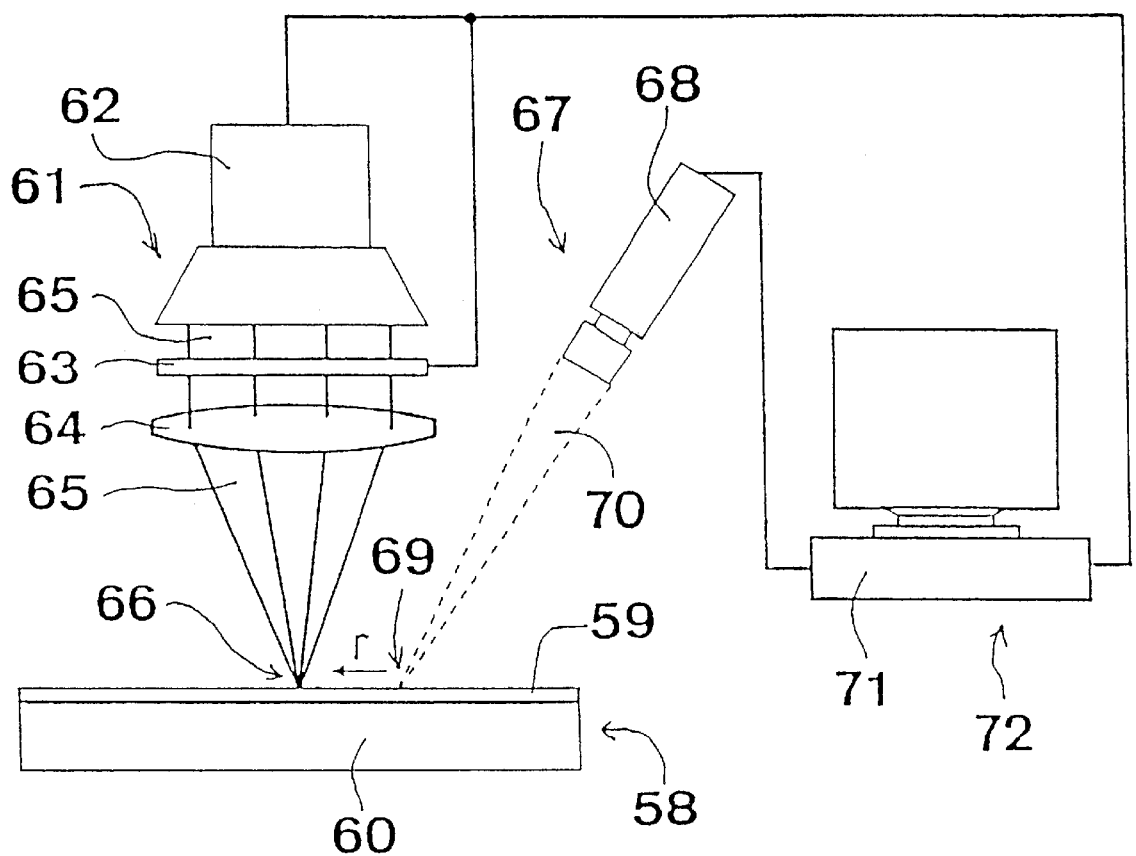
Figure 8:
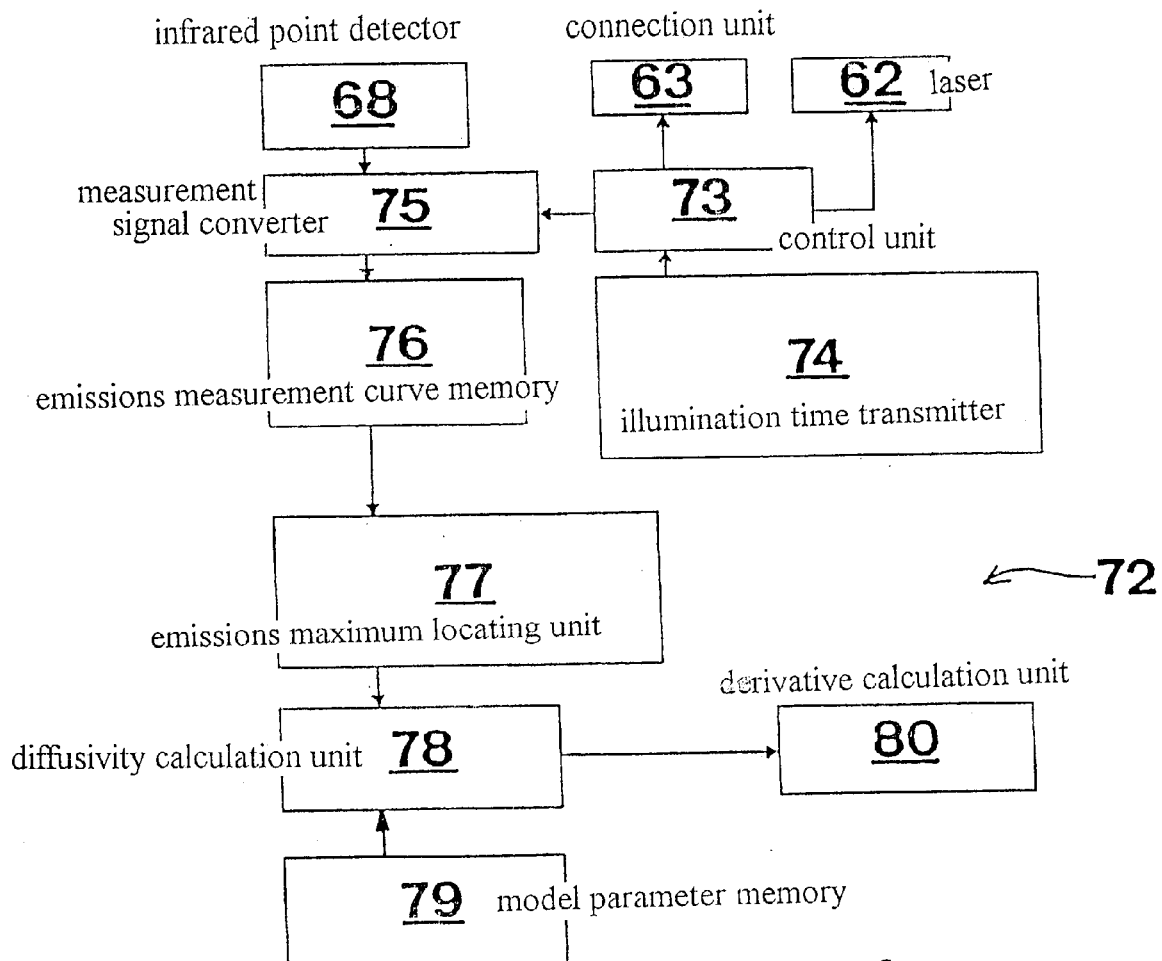

FIG. 7 is a schematic representation of another exemplary embodiment of a device for photothermally inspecting a test specimen, having an illumination device which focuses in a punctiform illumination region and having a detection device with a punctiform detection region spaced apart from the illumination region in the inspection of a test specimen; and FIG. 8 is a block circuit diagram of the device according to FIG. 7.

Figure 1:
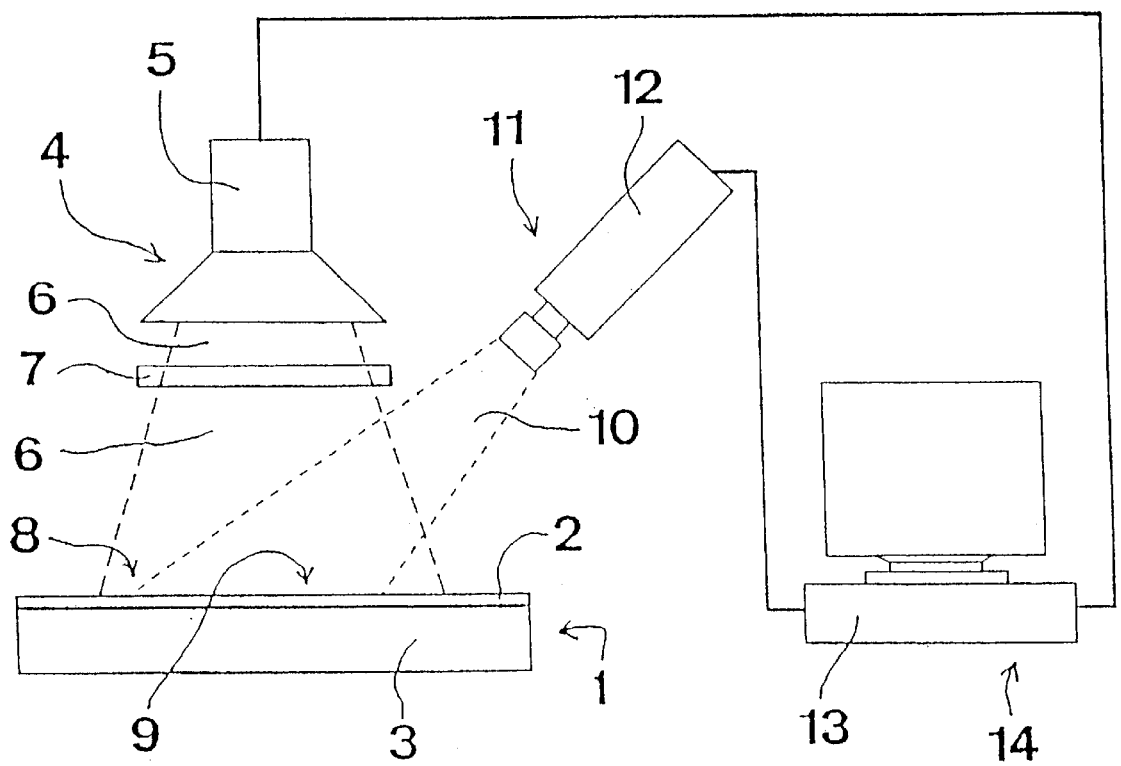
FIG. 1 is a schematic representation of an exemplary embodiment of a device according to the invention, in the inspection of a test specimen, having a detection device with an infrared camera.

FIG. 1 is a schematic representation of an exemplary embodiment of a device according to the invention for photothermally inspecting a test specimen 1, which is comprised of a substrate 3 provided with a thin coating 2. The coating 2 has a layer thickness which is constituted by the distance between two boundary surfaces of the coating 2. The device according to FIG. 1 has an illumination device 4 which has a flash bulb 5 as an adjustable illumination unit, with an illumination time of $t_P$. The flash bulb 5 can emit short, pulse-like flashes of light, preferably with intense spectral components in the visible spectral range, wherein the illumination time $t_P$ is shorter than the travel time of thermal waves through the coating 2 to the boundary surface adjacent to the test specimen 1. This corresponds to the quotient of the square of a value of a layer thickness of the coating 2 constituted by the distance between boundary surfaces and a value for the diffusivity between the boundary surfaces. After passing through an infrared filter 7 for absorbing infrared spectral components, the flashes of light act on the test specimen 1 as luminous radiation 6, essentially with their spectral components in the visible spectral range in an illumination region 8 that is spread out flat in this exemplary embodiment, and strike against the coating 2.

Depending on the absorption coefficient, the energy of the luminous radiation 6 is absorbed with a value preferably close to 1 in the illumination region 8, wherein a part of the absorbed energy is given off again as thermal radiation in the infrared spectral range. In order to detect a part of the thermal radiation 10 that lies within the illumination region 8 in a detection region 9, the device according to FIG. 1 has a detection device 11 with a local resolution infrared camera 12.

Furthermore, the device according to FIG. 1 is equipped with a control and evaluation device 14, which is embodied as a workstation 13, to which the flash bulb 5 and the infrared camera 12 are connected.

Figure 2:
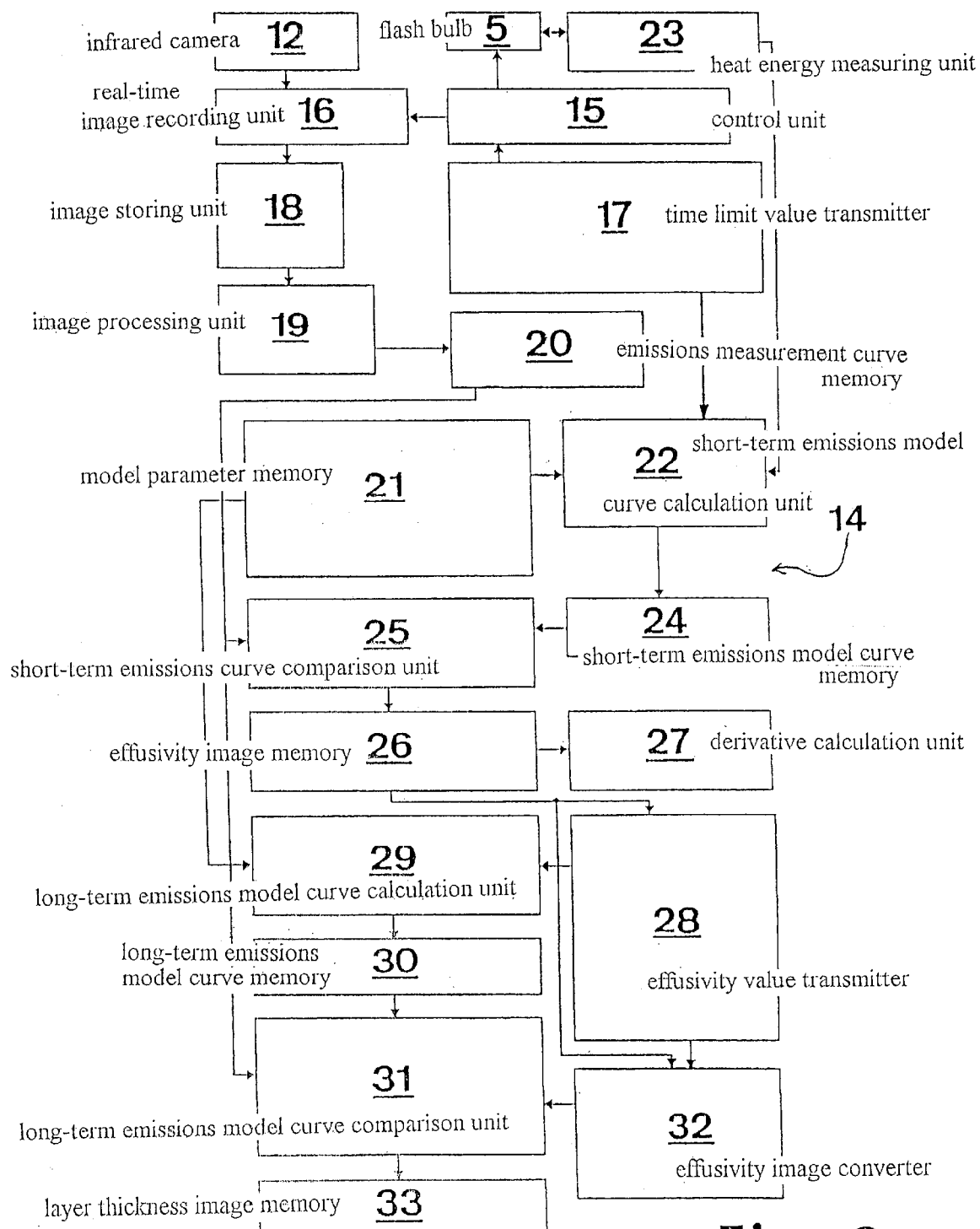
FIG. 2 is a block circuit diagram of the device according to FIG. 1.

In a block circuit diagram, FIG. 2 particularly shows the control and evaluation device 14 in the exemplary device according to FIG. 1. The control and evaluation device 14 has a control unit 15 to which are connected the flash bulb 5, a real-time image recording unit 16 that is connected to the infrared camera 12 and has a dynamic range of 12 bits and a time resolution of typically better than a few milliseconds, and a time limit value transmitter 17. The time limit value transmitter 17 can be used to supply the control unit 15 with the illumination time $t_P$, an image recording time as an end point $t_E$, and an effusivity evaluation time $t_A$, wherein the image recording time is used to determine the total duration of the recording of an emissions curve and the effusivity evaluation time $t_A$ is used to determine the time since the beginning of the illumination, which establishes the limit of the early cooling part of the emissions curve immediately following a heating part in order to determine the effusivity. The illumination time $t_P$ suitably corresponds to approximately half the time from the beginning of the illumination to the effusivity evaluation time $t_A$. For example, the image recording time is provided as ten times the value that is produced from the quotient of the square of an estimated value for a layer thickness and an estimated value for a diffusivity of the coating 2. It is suitable to select half of this quotient as the effusivity evaluation time $t_A$.

The output data of the real-time image recording unit 16 can be supplied to an image storing unit 18 in which a number of images of the detection region 9 can be stored in a chronological sequence, wherein the number of images that can be stored is as high as possible for a high time resolution. Suitable image numbers are from several tens to a few thousand images in a typical local resolution of 128×128 pixels. The image storing unit 18 is connected to an image processor unit 19, with which the data associated with the thermal radiation 10 emitted from the detection region 9 can preferably be detected for all of the pixels, but also for example, for image sections in the chronological course as emissions measurement curves. The emissions measurement curves can be stored in an emissions measurement curve memory 20.

Furthermore, the control and evaluation device 14 has a model parameter memory 21 which can store the thermal conductivity, density, specific heat capacity, and thickness of the substrate 3 of the test specimen 1 according to FIG. 1, as parameters for a calculation of emissions model curves, and can also suitably store an estimated value for the layer thickness of the coating 2 and an estimated value for the effusivity of the coating 2 of the test specimen 1. A short-term emissions model curve calculation unit 22 is connected to the model parameter memory 21. The short-term emissions model curve calculation unit 22 is connected to a heat energy measuring unit 23 which can establish a heat energy measuring parameter value associated with the illumination energy acting on the test specimen 1. With variation of the model parameter for the effusivity in the vicinity of its estimated value in the time range up until the effusivity evaluation time $t_A$ stored in the time limit value transmitter 17, including the heat energy measurement parameter value, the short-term emissions model curve calculation unit 22 can calculate a number of emissions model curves. The short-term emissions model curves calculated with the short-term emissions model curve calculation unit 22 can be stored in a short-term emissions model curve memory 24.

The control and evaluation device 14 also has the short-term emissions curve comparison unit 25, which can be acted on by the emissions measurement curves that can be stored in the emissions measurement memory 20 and by the short-term emissions model curves that can be stored in the short-term emissions model curve memory 24. By means of a comparison procedure, for example in accordance with the method of the smallest squares in the time range up until the effusivity evaluation time, the short-term emissions curve comparison unit 25 can determine the short-term emissions model curves which best agree with the emissions measurement curves of the detected pixels of the detection region 9 within the time range up until the effusivity evaluation time. The effusivity values that form the basis for the calculation of the best adapted short-term emissions model curves can be stored in an effusivity image memory 26 as an effusivity image of the detection region 9.

A derivative calculation unit 27 is connected to the effusivity image memory 26 and can be used to determine the thermal conductivity at a point on the coating 2 and the product of the density and the specific heat capacity at this point on the coating 2 of the test specimen 1 based on the value for the effusivity and a value for the diffusivity, which can be determined, for example, in accordance with the exemplary embodiment explained below in conjunction with FIG. 7. Furthermore, the effusivity image memory 26 is connected to an effusivity value transmitter 28 which can be used to determine the minimum and the maximum of the effusivity values stored in the effusivity image memory 26 and can be used to calculate a number of intermediate effusivity values, preferably spaced evenly apart from one another, between the minimal effusivity value and the maximal effusivity value.

The effusivity value transmitter 28 is connected to a long-term emissions model curve calculation unit 29, which can also be supplied with the model parameters of the model parameter memory unit 21. With variation of the layer thickness in the vicinity of the estimated values, in the time range between the effusivity evaluation time $t_A$ and the end point of the image recording time, the long-term emissions model curve calculation unit 29 can calculate long-term emissions model curves for each intermediary effusivity value as well as the minimal and maximal effusivity value and these long-term emissions model curves can be stored in a long-term emissions model curve memory 30 disposed after the long-term emissions model curve calculation unit 29.

The memory unit of the long-term emissions model curve memory 30 can be output to a long-term emissions model curve comparison unit 31, which is also connected to the emissions measurement curve memory 20 and an effusivity image converter 32. The effusivity image converter 32 is in turn connected to the effusivity image memory 26 and the effusivity value transmitter 28. Through the use of the effusivity image converter 32, the effusivity value at each pixel of the detection region 9 can be assigned the intermediary value or the minimal or maximal effusivity value of the effusivity value transmitter 28 that is disposed closest to this effusivity value in the relevant pixel.

With the long-term emissions curve comparison unit 31, a comparison procedure, for example in accordance with the method of the smallest squares, can determine the layer thickness value for each pixel, by means of which the best agreement between the relevant emissions measurement curve of this pixel and the corresponding long-term emissions model curves is produced based on the converted effusivity value from the effusivity image converter 32. The layer thickness values, which are determined with the long-term emissions curve comparison unit 31, in each of the pixels of the detection region 9 can be stored in a layer thickness image memory 33.

The memory contents of the effusivity image memory 26 as well as the layer thickness image memory 33 can be output, for example graphically, in a gray-value or color encoding by means of an output unit, not shown in FIG. 1, which belongs to the control and evaluation device 14, for example in the form of a display screen or printer.

The device explained by way of example in conjunction with FIG. 1 and FIG. 2 is particularly suitable for an essentially adjustment-free, local resolution determination of effusivity, which is particularly precise due to the comparison procedure that compares emissions measurement curves with emissions model curves in the short-term range up until the effusivity evaluation time $t_A$, and, through the comparison of emissions measurement curves and emissions model curves in the long-term range between the effusivity evaluation time and the end of the image recording time, is also particularly suitable for a very exact local resolution determination of the layer thickness of the coating 2 of the test specimen 1.

Figure 3:
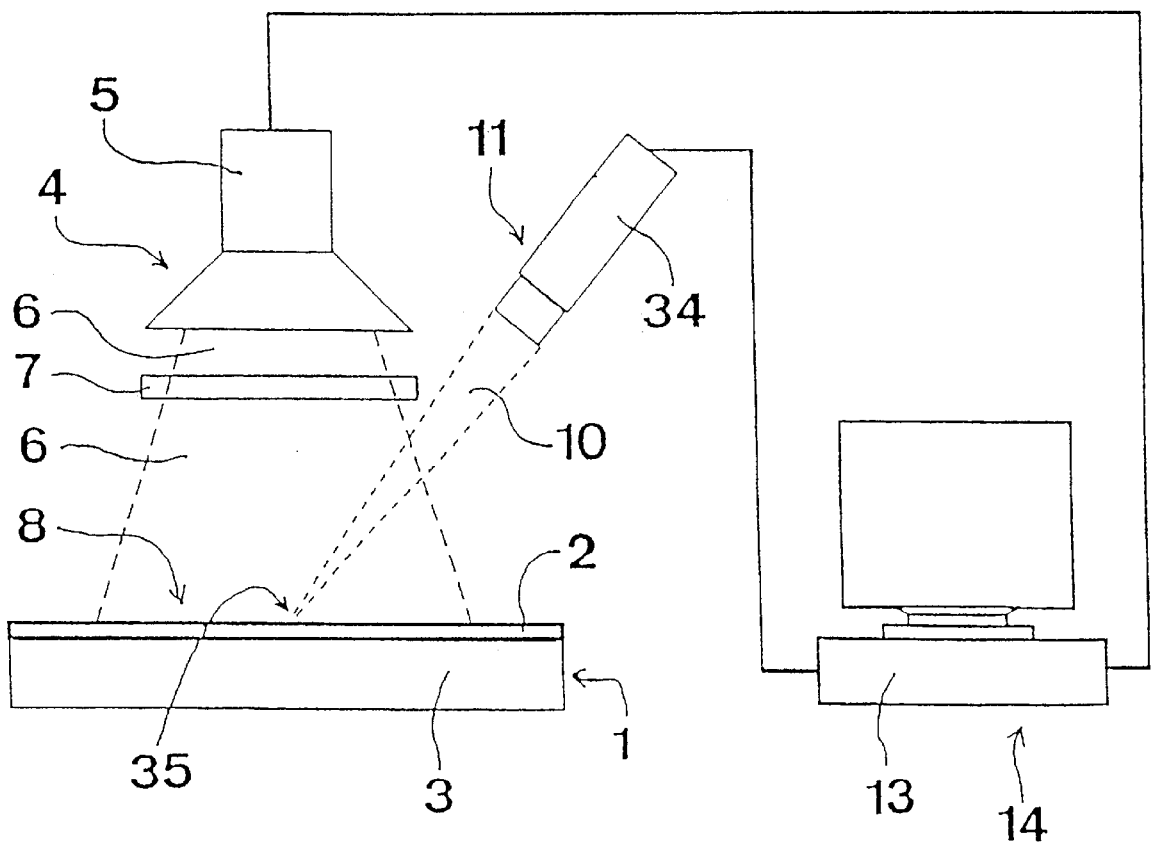
FIG. 3 is another exemplary embodiment of a device according to the invention, having a detection device with a one-cell infrared detector.

In a schematic representation, FIG. 3 shows another exemplary embodiment of a device for photothermally inspecting a test specimen 1, which is designed similarly to the exemplary embodiment explained in conjunction with FIG. 1, with the exception of the detection device 11. Correspondingly, the components which correspond in the exemplary embodiments according to FIG. 1 and FIG. 3 are provided with the same reference numerals and are not explained in further detail. In the exemplary embodiment according to FIG. 3, the detection device 11 is embodied as a one-cell infrared point detector 34 which can be used for time-resolved detection of thermal radiation 10 from a quasi-punctiform detection region 35 that is disposed inside the illumination region 8 and is very small in relation to the illumination region 8.

Figure 4:
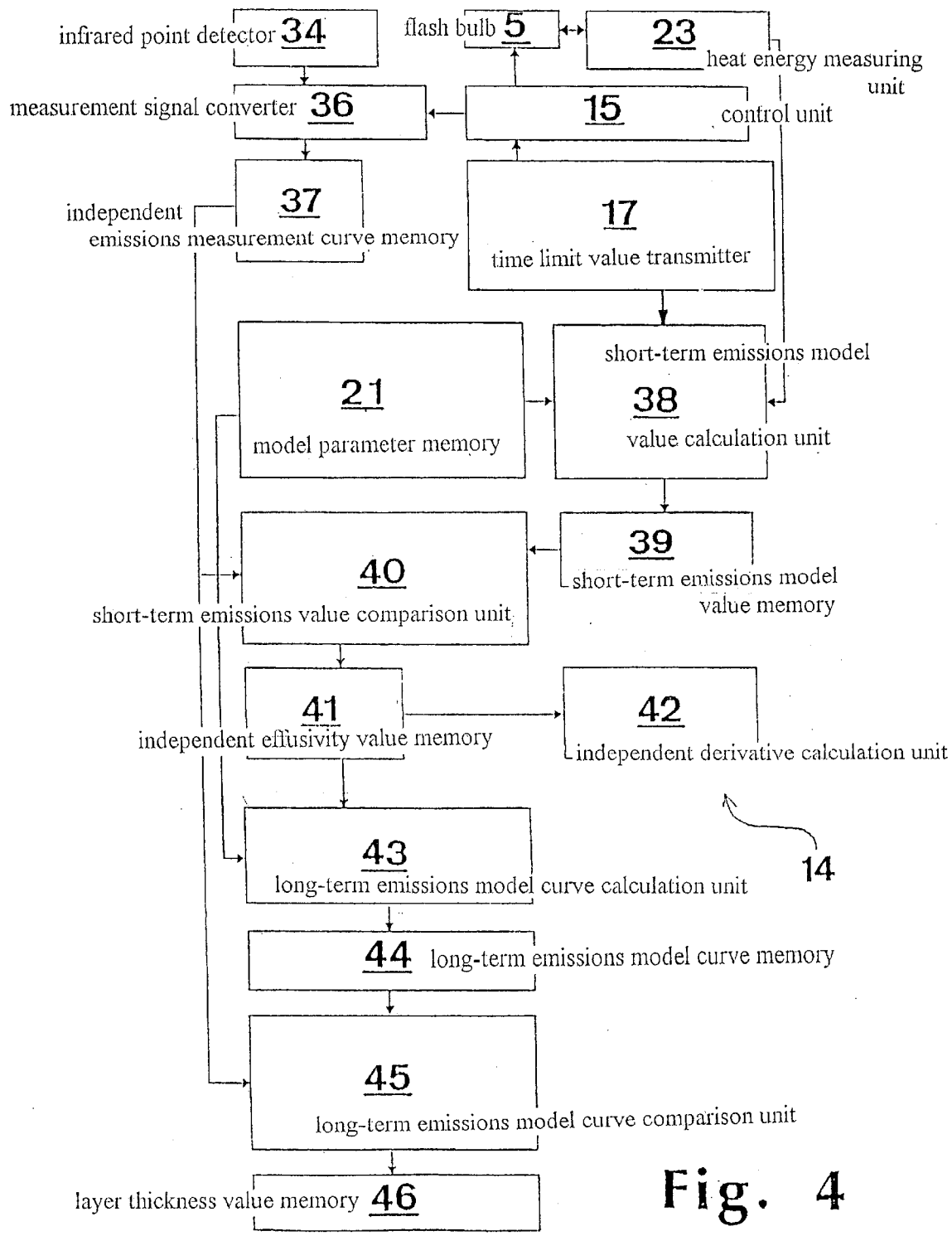
FIG. 4 is a block circuit diagram of the device according to FIG. 3.

FIG. 4 shows a block circuit diagram of the device according to FIG. 3, wherein in the embodiments of the control and evaluation device 14 according to FIG. 2 and FIG. 4, corresponding components are provided with the same reference numerals and are not explained in further detail.

The infrared point detector 34 is connected to a measurement signal converter 36, which in turn is controlled by the control unit 15. The thermal radiation 10 from the punctiform detection region 35 detected by the infrared point detector 34 can be stored in a time-resolved fashion as an independent emissions measurement curve in an independent emissions measurement curve memory 37 connected to the measurement signal converter 36.

The model parameter memory 21 is connected to a short-term emissions model value calculation unit 38 which is itself in turn connected to the time limit value transmitter 17 and the heat energy measuring unit 23. At a determination time $t_B$, the short-term emissions model value calculation unit 38 can be used to calculate the temperatures prevailing at this determination time $t_B$—as emissions model values— as a function of the effusivity, when there is variation of the effusivity in the vicinity of the estimated effusivity value, while taking into consideration the heat energy acting on the test specimen 1 as well as the model parameters from the model parameter memory 21, wherein the determination time $t_B$ is less than the effusivity evaluation time $t_A$. For example, the determination time $t_B$ is approximately half the time which has elapsed since the beginning of the illumination of the test specimen 1 up until the effusivity evaluation time $t_A$. The short-term emissions model value calculation unit 38 is followed by a short-term emissions model value memory 39 in which the emissions model values calculated at the determination time $t_B$ can be stored.

The control and evaluation device 14 according to FIG. 4 also has a short-term emissions value comparison unit 40, which is connected to the short-term emissions model value memory 39 and the independent emissions measurement curve memory 37 and, in accordance with the function of the short-term emissions curve comparison unit 25 according to FIG. 2, can be used to determine an independent effusivity model value for the detection region 35 at the determination time $t_B$ from the emissions model value with the least deviation from the emissions measurement value of the independent emissions measurement curve, and this independent effusivity model value can be stored in an independent effusivity value memory 41.

The independent effusivity value of the independent effusivity value memory 41 can be supplied to an independent derivative calculation unit 42 for calculating the thermal conductivity and the product of the density and the specific heat capacity in accordance with the function of the derivative calculation unit 27.

The independent effusivity value memory 41 and the model parameter memory 21 are followed by a long-term emissions model curve calculation unit 43 and, when there is variation of the layer thickness of the coating 2 in the vicinity of its estimated value and the effusivity value stored in the independent effusivity value memory 41, this long-term emissions model curve calculation unit 43 can be used to calculate long-term emissions model curves in a time range between the effusivity evaluation time $t_A$ and the end point $t_E$ of the measurement duration. The long-term emissions model curves calculated by means of the long-term emissions model curve calculation unit 43 can be supplied to a long-term emissions model curve memory 44, which is followed by a long-term emissions curve comparison unit 45.

With the long-term emissions curve comparison unit 45 that is also connected to the independent emissions measurement curve memory 37, in a comparison procedure—for example in accordance with the method of the smallest squares within the time range between the effusivity evaluation time $t_A$ and the end point $t_E$ of the measurement duration—the layer thickness of the coating 2 in the relevant pixel can be determined based on the best agreement of a long-term emissions model curve with the emissions measurement curve in the corresponding time range. The layer thickness value determined by means of the long-term emissions curve comparison unit 45 can be stored in a subsequent layer thickness value memory 46 and can be output, for example, by means of a display screen or printer, not shown in FIG. 4, that is part of the control and evaluation device 14.

The exemplary embodiment according to FIG. 3 and FIG. 4 can be used in a particularly suitable manner if a particularly rapid determination of the effusivity and the layer thickness must be carried out in a punctiform detection region 35.

Figure 5:
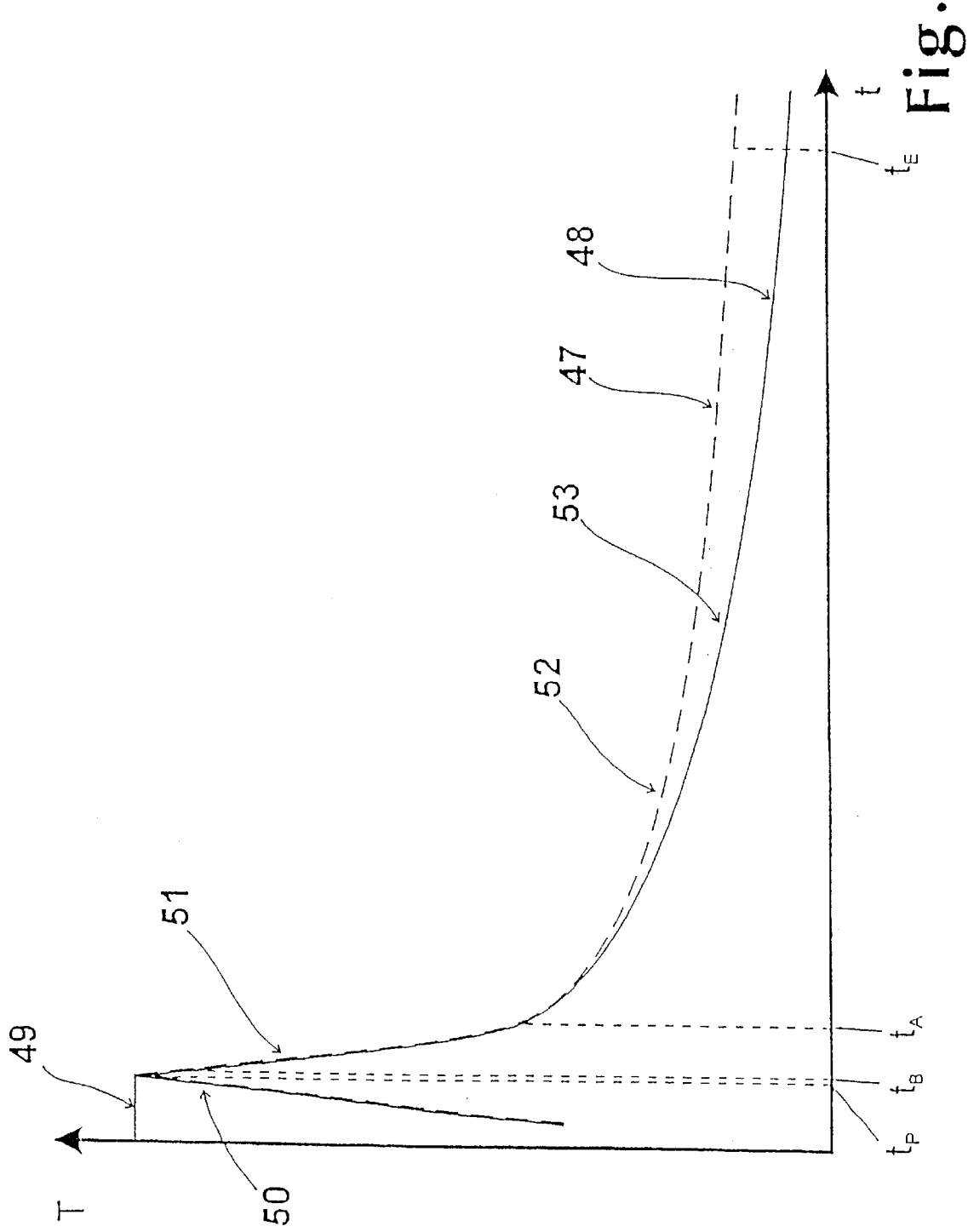
FIG. 5 shows emissions curves of test specimens with coatings of the same material composition, but with different layer thicknesses.

By way of example, FIG. 5 shows a graph of a first emissions model curve 47 and a second emissions model curve 48 of the kind produced according to numerical model calculations in a partial region of the detection region 9 or in a punctiform detection region 35 after illumination with short flashes of light 49 from the illumination unit that is embodied as a flash bulb 5. In the graph according to FIG. 5, the chronological course of the amplitude of the emissions model curves 47, 48 is plotted in this representation as temperature "T" along a time axis "t". The illumination time $t_P$ of the flash of light 49 is equal to the heating time of the heating part 50 of the two emissions model curves 47, 48 that increase up to a maximal temperature. In addition to the section 51 of the cooling parts 52, 53 that follow the heating part 50 and continue until the effusivity evaluation time $t_A$, the heating time 50 can also be used to determine the effusivity.

It is also clear from FIG. 5 that the section 51 of the cooling parts 52, 53 that immediately follows the heating part 50 is essentially congruent to model emissions curves 47, 48 associated with different layer thicknesses of coatings 2 so that with an evaluation of emissions measurement curves up until the effusivity evaluation time $t_A$, at least in conjunction with a measurement value and at least one associated emissions model value, the effusivity can be determined independently of the layer thickness of the coatings 2.

Furthermore, with an evaluation of the emissions measurement curves between the effusivity evaluation time $t_A$ and the end point $t_E$ of the image recording time, when there is a previously established effusivity value, the layer thickness of the coating 2 of the test specimen 1 can be precisely determined from the then mutually divergent courses of the cooling parts 52, 53 of the emissions model curves 47, 48, by means of comparison with the emissions measurement curves.

Figure 6:
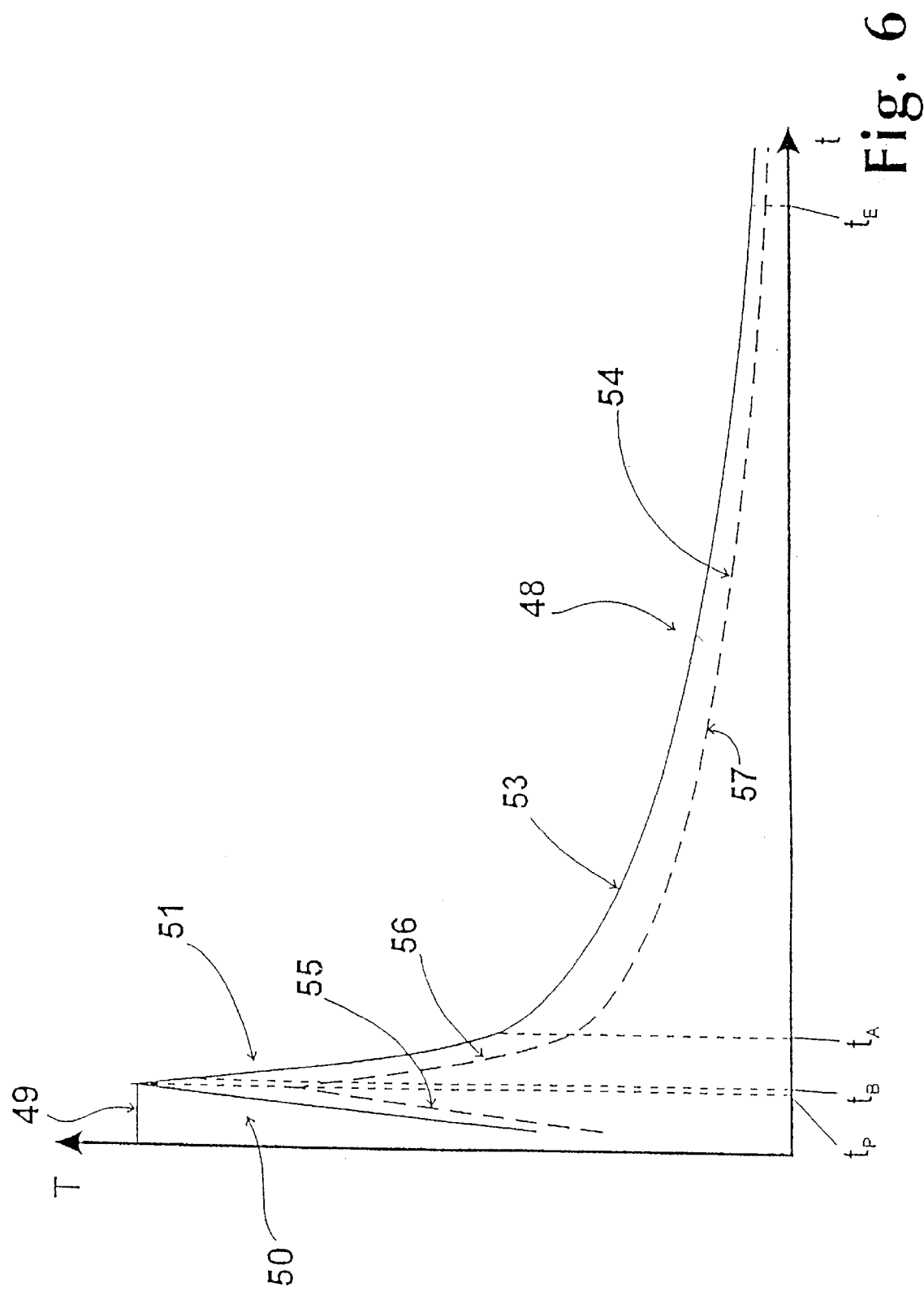
FIG. 6 shows emissions curves of test specimens with coatings of different material compositions, but with the same layer thickness.

In a graph, FIG. 6 shows the second emissions model curve 48 according to FIG. 5, in comparison with a third emissions model curve 54, wherein the emissions model curves 48, 54 shown in FIG. 6 each have a test specimen 1 with the same substrate 3 and the same layer thickness of a coating 2, but are made up of different materials. Due to the different materials of the coatings 2 and the as a rule different associated effusivities, a heating part 55, a section immediately following the heating part 55, and also section 56 of the remaining course of cooling part 57 of the third emissions model curve 54 are different from the course of the second emissions model curve 48. As a result, different materials of a coating 2 of a test specimen 1 can be determined by means of their different effusivities.

FIG. 7 is a schematic depiction of another exemplary embodiment of a device for photothermally inspecting a test specimen 58, which is made up of a substrate 60 provided with a coating 59. The device according to FIG. 7 has an illumination device 61, which has a laser 62 that emits continuously, preferably in the visible spectral range, as a radiation source. The laser 62 is followed by a shutter unit 63 as well as set of focusing optics 64 which, when the shutter unit 63 is open, can be used to focus luminous radiation 65 emitted by the laser 62 onto the coating 59 of the test specimen 58 in a punctiform illumination region 66.

Furthermore, the device according to claim 7 has a detection device 67 with a one-cell infrared point detector 68. The infrared point detector 68 is equipped with a punctiform detection region 69 in a central spacing r indicated with an arrow, as a distance from the punctiform illumination region 66 in order to detect thermal radiation 70 emitted from the detection region 69.

The device according to FIG. 7 is equipped with a control and evaluation device 72 that is embodied, for example, as a workstation 71, to which are connected the laser 62, the connecting unit 63, and the infrared point detector 68 in order to control the illumination, detect thermal radiation 70, and carry out evaluations.

FIG. 8 is a block circuit diagram of the device according to FIG. 7, particularly showing the design of the control and evaluation device 72. The control and evaluation device 72 has a control unit 73 which, in order to control an illumination time, can be supplied with control data associated with at least two illumination times from an illumination time transmitter 74. For example, a shorter first illumination time corresponds to a quarter of the quotient of the square of an estimated value for a layer thickness of the coating 59 and an estimated value for a diffusivity of the coating 59, and a longer second illumination time corresponds to half of this quotient. The connection unit 63 can be correspondingly actuated with the illumination times transmitted from the illumination time transmitter 74. Furthermore, the laser 62 is connected to the control unit 73 for function monitoring.

For the purpose of digitized data reception, the infrared point detector 68 is followed by a measurement signal converter 75 which is likewise connected to the control unit 73 for cyclical signal conversion. The output data of the measurement signal converter 75 associated with each illumination time, which correspond to the chronological course of the intensity of thermal radiation 70—typically characterized by an associated temperature value—from the detection region 69 disposed at a diffusion distance r from the illumination region 66, can be stored as emissions measurement curves in an emissions measurement curve memory 76.

The emissions measurement curves that can be stored in the emissions measurement curve memory 76 can be transmitted to an emissions maximum locating unit 77 which, for each emissions measurement curve, can determine a maximal temperature associated with the maximum emission after the beginning of the illumination and which can determine the time of the maximal emission by directly evaluating the emissions measurement curve or alternatively through the input of an illumination time. The control and evaluation device 72 also has a diffusivity calculation unit 78, which is connected, on the one hand, to the emissions maximum locating unit 77 and, on the other hand, to a model parameter memory 79. The model parameter memory 79 can store the central spacing r between the punctiform illumination region 66 and the punctiform detection region 69 as well as an estimated value for the diffusivity. With the diffusivity calculation unit 78, through the use of a numerical process, for example the Newton process, the diffusivity of the coating 59 can be determined by varying the estimated value for the diffusivity in the aboveindicated equation (2).

In addition, the control and evaluation device 72 has a derivative calculation unit 80 which is connected to the diffusion calculation unit 78. In addition to the determined diffusivity and the effusivity determined, for example, by means of one of the abovementioned devices according to FIG. 1 and FIG. 2 or FIG. 3 and FIG. 4, the derivative calculation unit 80 can also determine the thermal conductivity as well as the product of the density and the specific heat capacity of the coating 59.

Naturally, the detection device 67 according to FIG. 7 can also be equipped with a linear infrared camera or an area-detecting infrared camera.

What is claimed is:

1. Process for photothermally inspecting a test specimen in which the test specimen (58) is acted on by luminous radiation (65) in an illumination region (66) during an illumination time and thermal radiation (70) emitted by the test specimen (58) from a detection region (69) is detected, wherein properties of the test specimen (58) are determined from the chronological course of the thermal radiation (70), which can be represented by means of an emissions curve that has a heating part with an increasing amplitude and a cooling part with a decreasing amplitude, characterized in that at least two illumination times ($t_p$) are adjusted, which are less than the quotient of the square of an estimated value of a layer thickness constituted by the distance between boundary surfaces and an estimated value for the diffusivity between the boundary surfaces, in that the illumination region (66) and the detection region (69) are spaced apart from each other with a diffusion spacing, in that the maximal amplitudes are determined for each emissions curve, which maximal amplitudes occur for each illumination time in the detection region, with associated adjustment times, and in that the diffusivity is determined from the ratio between at least two maximal amplitudes, the diffusion spacing, and the associated adjustment times.

2. Process according to claim 1, characterized in that each illumination time corresponds to at most half of the quotient.

3. Process according to claim 2, characterized in that the diffusivity of a coating (59) of the test specimen (58) is determined.

4. Device for photothermally inspecting a test specimen, in particular by carrying out a process according to claim 2, having an illumination device (61, 62) which can act on a test specimen (1) with luminous radiation (65) in an illumination region (66) during an illumination time, having a detection device (67, 68) which can carry out a time-resolved detection of thermal radiation (70) emitted by the test specimen (58) from a detection region (69), and having a control and evaluation device (72) which can determine properties of the test specimen (58) from the chronological course of the thermal radiation (70), which can be represented by means of an emissions curve that has a heating part with an increasing amplitude and a cooling part with a decreasing amplitude, characterized in that the illumination device (61, 62, 63) can set at least two illumination times, which are less than the quotient of the square of an estimated value of a layer thickness constituted by the distance between boundary surfaces and an estimated value for the diffusivity between the boundary surfaces, in that the illumination region (66) and the detection region (69) are spaced apart from each other with a diffusion spacing (r), in that an emissions maximum locating unit (77) can determine maximal amplitudes of each emissions curve which occur for each illumination time in the detection region (69), with associated adjustment times, and in that a diffusivity calculation unit (78) can determine a diffusivity from the ratio between two maximal amplitudes, the diffusion spacing, and the associated adjustment times.

5. Process according to claim 2, characterized in that the product of the density and the specific heat capacity as well as a thermal conductivity are determined from the diffusivity and an effusivity which is in particular determined in accordance with a process for photothermally inspecting a test specimen in which the test specimen is acted on by luminous radiation in an illumination region during an illumination time and thermal radiation emitted by the test specimen from a detection region is detected in a time-resolved manner, wherein properties of the test specimen are determined from the chronological course of the thermal radiation, which can be represented by means of an emissions curve, which has a heating part with an increasing amplitude and a cooling part with a decreasing amplitude, characterized in that an illumination time is adjusted, which is less than the quotient of the square of an estimated value of a layer thickness constituted by the distance between boundary surfaces and an estimated value for the diffusivity between the boundary surfaces, and that the effusivity of the test specimen is determined from at least one measurement value disposed in the heating part or in a section of the cooling part immediately following the heating part, which has a high cooling rate that corresponds to a heating rate of the heating part.

6. Process according to claim 1, characterized in that the diffusivity of a coating (59) of the test specimen (58) is determined.

7. Device for photothermally inspecting a test specimen, in particular by carrying out a process according to claim 1, having an illumination device (61, 62) which can act on a test specimen (1) with luminous radiation (65) in an illumination region (66) during an illumination time, having a detection device (67, 68) which can carry out a time-resolved detection of thermal radiation (70) emitted by the test specimen (58) from a detection region (69), and having a control and evaluation device (72) which can determine properties of the test specimen (58) from the chronological course of the thermal radiation (70), which can be represented by means of an emissions curve that has a heating part with an increasing amplitude and a cooling part with a decreasing amplitude, characterized in that the illumination device (61, 62, 63) can set at least two illumination times, which are less than the quotient of the square of an estimated value of a layer thickness constituted by the distance between boundary surfaces and an estimated value for the diffusivity between the boundary surfaces, in that the illumination region (66) and the detection region (69) are spaced part from each other with a diffusion spacing (r), in that an emissions maximum locating unit (77) can determine maximal amplitudes of each emissions curve which occur for each illumination time in the detection region (69), with associated adjustment times, and in that a diffusivity calculation unit (78) can determine a diffusivity from the ratio between two maximal amplitudes, the diffusion spacing, and the associated adjustment times.

8. Device according to claim 7, characterized in that the illumination region (69) and preferably also the detection region (66) are punctiform.

9. Device according to claim 7, characterized in that each illumination time corresponds to at most half of the quotient of the square of an estimated value for the layer thickness of a coating (59) of the test specimen (58) and an estimated value of the diffusivity of the coating (2).

10. Device according to claim 7, characterized in that the shorter illumination time is approximately half as long as the longer illumination time.

11. Device for photothermally inspecting a test specimen, in particular by carrying out a process for photothermally inspecting a test specimen in which the test specimen is acted on by luminous radiation in an illumination region during an illumination time and thermal radiation emitted by the test specimen from a detection region is detected in a time-resolved manner, wherein properties of the test specimen are determined from the chronological course of the thermal radiation, which can be represented by means of an emissions curve, which has a heating part with an increasing amplitude and a cooling part with a decreasing amplitude, characterized in that an illumination time is adjusted, which is less than the quotient of the square of an estimated value of a layer thickness constituted by the distance between boundary surfaces and an estimated value for the diffusivity between the boundary surfaces, and that the effusivity of the test specimen is determined from at least one measurement value disposed in the heating part or in a section of the cooling part immediately following the heating part, which has a high cooling rate that corresponds to a heating rate of the heating part, the device having an illumination device which can act on the test specimen with luminous radiation in an illumination region during an illumination time, having a detection device which can carry out a time-resolved detection of thermal radiation emitted by the test specimen from a detection region, and having a control and evaluation device which can determine properties of the test specimen from the chronological course of the thermal radiation, which can be represented by means of an emissions curve, which has a heating part with an increasing amplitude and a cooling part with a decreasing amplitude, characterized in that the illumination device can be used to adjust at least one illumination time, which is less than the quotient of the square of an estimated value of a layer thickness constituted by the distance between boundary surfaces and an estimated value for the diffusivity between the boundary surfaces, and that a calculation unit is provided, which can be used to determine the effusivity of the test specimen from at least one measurement value disposed in the heating part or in a section of the cooling part immediately following the heating part, which has a high cooling rate that corresponds to a heating rate of the heating part, characterized in that the detection unit can be used to detect a number of measurement values disposed in the heating part and/or in the section of the cooling part of the emissions curve immediately following the heating part, further characterized in that a model parameter memory is provided, which can store as parameters predetermined values for a thermal conductivity and the product of density and specific heat capacity of a substrate, as well as an estimated value for an effusivity and an estimated value for a layer thickness of a coating of the test specimen, in that a heat energy measuring unit is provided, which can establish a heat energy measuring parameter value associated with the energy of the luminous radiation acting on the test specimen, in that a short-term emissions model curve calculation unit is provided with which initial emissions model curves—which contain measurement values that are established for determining the effusivity—can be calculated by means of the heat energy measurement parameter value and the other predetermined parameters, with variation of the effusivity in the vicinity of the associated estimated value in at least one of the sections of the emissions curves, and that a short-term emissions curve comparison unit can determine the initial emissions model curve, which can be determined with the corresponding effusivity and has the least deviations from the measurement values.

12. Device for photothermally inspecting a test specimen, in particular by carrying out a process for photothermally inspecting a test specimen in which the test specimen is acted on by luminous radiation in an illumination region during an illumination time and thermal radiation emitted by the test specimen from a detection region is detected in a time-resolved manner, wherein properties of the test specimen are determined from the chronological course of the thermal radiation, which can be represented by means of an emissions curve, which has a heating part with an increasing amplitude and a cooling part with a decreasing amplitude, characterized in that an illumination time is adjusted, which is less than the quotient of the square of an estimated value of a layer thickness constituted by the distance between boundary surfaces and an estimated value for the diffusivity between the boundary surfaces, and that the effusivity of the test specimen is determined from at least one measurement value disposed in the heating part or in a section of the cooling part immediately following the heating part, which has a high cooling rate that corresponds to a heating rate of the heating part, the device having an illumination device which can act on the test specimen with luminous radiation in an illumination region during an illumination time, having a detection device which can carry out a time-resolved detection of thermal radiation emitted by the test specimen from a detection region, and having a control and evaluation device which can determine properties of the test specimen from the chronological course of the thermal radiation, which can be represented by means of an emissions curve, which has a heating part with an increasing amplitude and a cooling part with a decreasing amplitude, characterized in that the illumination device can be used to adjust at least one illumination time, which is less than the quotient of the square of an estimated value of a layer thickness constituted by the distance between boundary surfaces and an estimated value for the diffusivity between the boundary surfaces, and that a calculation unit is provided, which can be used to determine the effusivity of the test specimen from at least one measurement value disposed in the heating part or in a section of the cooling part immediately following the heating part, which has a high cooling rate that corresponds to a heating rate of the heating part, characterized in that the detection unit can be used to detect a number of measurement values disposed in the in the section of the cooling part immediately following the heating part, up to a multiple of the duration of the heating part, further characterized in that a long-term emissions model curve calculation unit is provided, which can use the predetermined parameters to calculate the sections of the cooling parts of a number of cooling model curves in which the measurement values lie, and that a long-term emissions curve comparison unit can determine the cooling model curve with the least deviations from the measurement values.

* * * * *